(12) United States Patent
Julin et al.

(10) Patent No.: US 6,391,641 B1
(45) Date of Patent: May 21, 2002

(54) TRANSLATIONALLY-COUPLED REPORTER GENE

(75) Inventors: Douglas A. Julin, Hyattsville; Jingdi Wang; Ruiwu Wang, both of College Park, all of MD (US)

(73) Assignee: University of Maryland, College Park, Riverdale, MD (US)

( * ) Notice: Subject to any disclaimer, the term of this patent is extended or adjusted under 35 U.S.C. 154(b) by 0 days.

(21) Appl. No.: 09/560,649

(22) Filed: Apr. 28, 2000

Related U.S. Application Data
(60) Provisional application No. 60/131,533, filed on Apr. 29, 1999.

(51) Int. Cl.[7] .............................................. C12N 15/63
(52) U.S. Cl. ......................... 435/471; 435/6; 435/69.1; 435/91.5; 435/440; 435/455
(58) Field of Search ............................. 435/6, 440, 91.4, 435/320.1

(56) References Cited

PUBLICATIONS

Sergey M. Podkovyrov et al, A new vector–host system for construction of lac Z transcriptional fusions where only low–level gene expression is desirable, Gene, 156 (1995) 151–152.*
New England Biolabs Catalog. Copyright 1996. p. 164.*
New England Biolabs Catalog. Copyright 1996. p. 204.*
Bernasconi et al. 1994. Functional expression of Arabidopsis thaliana anthranilate synthase subunit in *Escherichia coli*. Plant Physiol. 106: 353–358.*
Ishioka et al. 1997. Detection of heterozygous truncating mutations in the BRCA1 and APC genes by using a rapid screening assay in yeast. Proc. Natl. Acad. Sci. U.S.A. 94: 2449–2453.*

Korangy et al. 1992. Alteration by Site–directed mutagenesis of the conserved lysine residue in the ATP–binding consensus sequence of the RecD subunit of the *Escherichia coli* RecBCD enzyme. J. Biol. Chem. 267:1727–1732.*
Translational Reinitiation in the presence and absence of a shine and dalgarno sequence, Spanaard, Remco et al., *Nucleic Acids Research*, vol. 17, No. 14, pp.: 5501–5507, 1998.
Translation Through an uncDC mRNA Secondary Structure Governs the Level of uncC Expression in *Escherichia Coli*, Dallman, H. Garry, et al., Journal of Bacteriology, vol. 176, No. 5, pp. 1242–1250, Mar. 1994.
Effects of Intercistronic Length on the Efficiency of Reinitiation by Eucaryotic Ribosomes, Kozak, M., Molecular and Cellular Biology, vol. 7, No. 10, pp. 3438–3445, Oct. 1987.
Random Mutagenesis on the Pseudomonas Lipase activator protein, Lipb: Exploring Amino Acids Residues Required for its Function, Shibata, H. et al., Protein Eng. vol. 11, No. 6, pp. 467–472, 1998.
Direct Random Mutagenesis of Gene–Sized DNA Fragments Usning Polymerase Chain Reation, Fromant, M. et al., Anal. Biochem., 224, pp. 347–353, 1995.

* cited by examiner

*Primary Examiner*—George C. Elliott
*Assistant Examiner*—Bronwen M. Loeb
(74) *Attorney, Agent, or Firm*—McDermott, Will & Emery (57) ABSTRACT

A method of selecting for missense mutants that express a protein is disclosed. The method comprises constructing an operon comprising an upstream gene and a downstream reporter gene, wherein the upstream gene and the reporter gene are translationally coupled, wherein the reporter protein is expressed after the translation of the upstream gene. The method further comprises expressing the downstream reporter gene after introducing at least one mutation into the upstream gene. Finally, the mutants are screened for the ability to express the reporter protein, which is indicative of a missense mutant.

18 Claims, 2 Drawing Sheets

SEQUENCE LISTING

<160> NUMBER OF SEQ ID NOS: 2

<210> SEQ ID NO 1
<211> LENGTH: 26
<212> TYPE: DNA
<213> ORGANISM: synthetic construct

<400> SEQUENCE: 1
gaatgactct agaggaggtc atgagg                                          26

<210> SEQ ID NO 2
<211> LENGTH: 27
<212> TYPE: RNA
<213> ORGANISM: synthetic construct

<400> SEQUENCE: 2
gaaugacucu agaggagguc augaggc                                         27

TRANSLATIONALLY-COUPLED REPORTER GENE

CROSS REFERENCE TO RELATED APPLICATIONS

This application claims the benefit of priority of Provisional Application No. 60/131,533, filed Apr. 29, 1999.

GOVERNMENT INTEREST IN THE INVENTION

This invention was made with Government support under Grant No. GM39777 awarded by the National Institutes of Health. The Government has certain rights in this invention.

FIELD OF THE INVENTION

The present invention is in the field of mutagenesis and mutation detection. The invention is also related to a DNA construct in which at least two genes are translationally coupled. The invention is also related to a method of detecting missense mutations and eliminating nonsense mutations after a random mutagenesis procedure.

BACKGROUND OF THE INVENTION

Random mutagenesis of a cloned gene followed by phenotypic selection is a powerful tool for identifying amino acid residues or protein domains that are critical for protein function, particularly when specific residues that are likely to be mechanistically important cannot be identified by other means. Random mutations can be introduced into a specific gene or portion of a gene by a variety of methods, including PCR amplification under mutagenic conditions (Fromant, M., Blanquet, S., and Plateau, P. (1995) *Anal. Biochem.* 224, 347–353; Vartanian, J.-P., Henry, M., and Wain-Hobson, S. (1996) *Nucl. Acids Res.* 24, 2627–2631). However, a problem that can arise with this approach is that nonsense or frameshift mutations that give rise to a truncated protein may give the selected phenotype, but they are otherwise uninformative as to the specific residues that are required for activity. Moreover, a truncated mutant protein may be susceptible to proteolytic degradation in the cell (Gottesman, S., Wickner, S., and Maurizi, M. R. (1997) *Genes & Devel.* 11, 815–823) and thus may not be isolatable for further study. In some studies a large majority of mutants (80–90%) produced by random procedures encoded truncated or unstable proteins (Friedrich, T., Roth, M., Helm-Kruse, S., and Jeltsch, A. (1998) *Biol. Chem.* 379, 475–480; Kostelidou, K., Jagura-Burdzy, G.; and Thomas, C. M. (1998) *J. Mol. Biol.* 281, 453–463; van den Ent, F. M., Vos, A., and Plasterk, R. H. (1998) *J. Virol.* 72, 3916–3924; Shibata, H., Kato, H., and Oda, J. (1998) *Protein Eng.* 11, 467–472). Thus hundreds of colonies that expressed mutant protein had to be screened by relatively time consuming and labor intensive methods such as SDS-PAGE and/or western blot analysis to identify those that expressed full-length protein and were potential missense point mutants.

We sought an efficient way to winnow out nonsense mutations that produce truncated protein in the course of a random mutagenesis study of the RecD subunit of the RecBCD enzyme from *Escherichia coli*. For this purpose, we constructed a synthetic operon in which a reporter gene that encodes a selectable marker, the gene for kanamycin resistance (Oka, A., Sugisaki, H., and Takanami, M. (1981) *J. Mol. Biol.* 147, 217–226), is downstream of the recD gene. Translation of the kanamycin resistance gene, and therefore generation of a kanamycin resistant colony, should be dependent on complete translation of the upstream recD gene ()as, A., and Yanofsky, C. (1989) *Nucl. Acids Res.* 17, 9333–9340; Spanjaard, R. A., and van Duin, J. (1989) *Nucl. Acids Res.* 17 5501–5507). More than 90% of the random mutants obtained using this synthetic operon expressed full-length RecD protein. This approach may be of general use to practitioners of random mutagenesis.

SUMMARY OF THE INVENTION

The present invention has met the hereinbefore-described need.

It is an object of the present invention to provide a method of selecting for missense mutants that express a protein comprising:

constructing an operon comprising an upstream gene and a downstream reporter gene, wherein said upstream gene and said reporter gene are translationally coupled; wherein the reporter protein is expressed after the translation of the upstream gene, expressing the downstream reporter gene after introducing at least one mutation into the upstream gene, and screening for the mutant that expresses the reporter protein, which is indicative of said missense mutant.

In a preferred embodiment, the downstream reporter gene and the upstream gene are coupled via a ribosome-binding site. The reporter gene may encode a protein having virtually any detective property, which may include, but not limited to, ones that have fluorescent property, calorimetric property, or enzymatic property. Furthermore, reporter gene can be a selective marker gene, such as an antibiotic resistance gene or an auxotrophic marker.

The reporter gene, upstream gene, or both can be from any source expressed in any suitable vector in a transformed cell, such as an eucaryotic cell, including, but not limited to, mammalian or plant cell, or bacterial cell.

The mutation can be introduced by polymerase chain reaction or chemical mutagens, among other conventionally known methods.

The ribosome binding site can include but is not limited to the sequence 5'-AGGAGGU, 5'-GAGGGG, 5'-GGAG, 5'-GGUGGU, 5'-GGAGG or 5'-UAAGGAGGU. In addition, the ribosome binding site may form part of a stem and loop structure with a nearby sequence, wherein the stability of said stem and loop structure is optimized by arranging the complementarity in the stem structure so that a maximum number of base pairs is formed.

Another object of the invention is to provide a method for identifying and eliminating nonsense mutations in the upstream gene after mutagenizing comprising:

constructing an operon comprising a downstream reporter gene and an upstream gene, wherein the said reporter gene and the upstream gene are translationally coupled, wherein the reporter protein is expressed after the translation of the upstream gene, generating the random mutations in the upstream gene before or after said operon construct is made, expressing the downstream reporter gene after introducing at least one mutation into the upstream gene, and screening for the mutants by expressing the proteins.

It is still another object of this invention to provide a kit for determining the presence or absence of missense or nonsense mutations present on an upstream gene in a translationally coupled construct as desired. Each component of the kit(s) may be individually packaged in its own suitable container. The individual containers may also be labeled in a manner, which identifies the contents. Moreover, the individually packaged components may be placed in a larger container capable of holding all desired components. Associated with the kit may be instructions, which explain how to use the kit. These instructions may be written on or attached to the kit. Thus, the invention provides a kit for generating random mutations and for eliminating those that encode a truncated protein, comprising a vector constituting the translationally coupled operon described above, and instructions for carrying out the detection method.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein;

FIG. 2(B). RNA encoded by the linker between the 3' end of the recD gene and the start of the kan$^r$ gene in pHRecDkan. The hairpin structure shown has an estimated $\Delta G°=-6.2$ kcal/mol at 37° C. calculated from the known sequence-dependent thermodynamic parameters for base pair stabilities using the program MFOLD (Mathews, D. H., Sabina, J., Zuker M., and Turner, D. H. (1999) *J. Mol. Biol.* 288, 911–940, incorporated by reference herein in its entirety, and the related computer program which is at http://mfold2.wustl.edu/~mfold/rna/form1.cgi as of Apr. 27, 2000). The AUG start codon for kan$^r$ is circled.

DETAILED DESCRIPTION OF THE INVENTION

As used herein, "translational coupling" or "translationally-coupled" refers to a situation in which the coding information for at least two different proteins is contained within a single messenger RNA, and the cellular translation machinery (the ribosome) must completely translate the 5'-most gene or genes ("upstream" gene) before it can begin to translate the gene or genes situated towards the 3'-end of the MRNA (the "downstream" gene). The ribosome is unable to initiate translation of the downstream gene directly. Thus synthesis of the protein encoded by the downstream gene is said to be "translationally-coupled" to synthesis of the protein encoded by the upstream gene.

The system is not limited to the recD-kan$^r$ gene construct exemplified in the present application. It could be applied to random mutagenesis of any gene, for which a selection method can be devised, with any reporter gene (as defined below). The general method could be used for mutational analysis of genes expressed in other bacteria besides *Escherichia coli*, and in mammalian or plant cells since the translation of an upstream gene has been shown to affect translation of a downstream gene in some situations in those organisms as well (Kozak, M. (1987) *Mol. Cell Biol.* 7, 3438–3445; Scholthof, H. B., Gowda, S., Wu, F. C., Shepherd, R. J. (1992) *J. Virol.* 66, 3131–3139).

As used herein, "ribosome binding site" generally refers to the sequence 5'-AGGAGGU in the mRNA (coded by 5'-AGGAGGT in the DNA). The bacterial ribosome binds to this sequence in the mRNA during the initiation of translation. The ribosome-binding site is not limited to this particular sequence as certain sequence variations are natural ribosome binding sites in the cell. Some of the naturally-occurring sequence variations in *Escherichia coli*, for example, are: 5'-GAGGGG, 5'-GGAG, 5'-GGUGGU, 5'-GGAGG, and 5'-UAAGGAGGU (Nelson, D. L. and Cox, M. M. (2000) Lehninger Principles of Biochemistry,3$^{rd}$ edition, p. 1046, Worth Publishers, New York, N.Y., which is incorporated herein by reference in its entirety).

As used herein, "reporter gene" refers to a gene that encodes a protein the production and detection of which is used as a surrogate to detect indirectly the transcription or translation of a second gene or gene fragment. The reporter protein is that protein encoded by the reporter gene. Preferably, the reporter gene encodes an enzyme whose catalytic activity can be detected by a simple assay method or a protein with a property such as intrinsic fluorescence so that expression of the reporter gene can be detected in a simple and rapid assay requiring minimal sample preparation. More preferably, the reporter gene encodes an enzyme or protein, the expression of which in a particular bacterial colony or other cell can be detected by visual examination of the growth, color, or morphology of the colony or cells as they appear during growth on an agar plate or other culture medium. The reporter gene can also encode a selective marker such as an antibiotic resistance gene including but not limited to kanamycin-resistance gene, ampicillin-resistance gene, rifampicin-resistance gene, chloramphenicol-resistance gene, tetracycline-resistance gene, and so on. A protein encoded by an antibiotic resistance gene allows the cell to grow in the presence of that antibiotic. Only a cell that expresses the antibiotic resistance gene (i.e., the gene is both transcribed and translated) is able to grow and form a colony; non-expressing cells are killed by the antibiotic.

As used herein, a "prokaryotic gene" means a gene that is transcriptionally and translationally expressed in a prokaryote cell. Similarly, by an "eukaryotic gene", "mammalian gene", and "plant gene", it is meant that such gene is expressed in each specified cell type. In the same way, "prokaryotic promoter", "eukaryotic promoter", "mammalian promoter", "plant promoter" and so on refer to promoter elements that are functional in the cell type descriptor.

The DNA is readily modified by substitution, deletion or insertion of nucleotides, thereby resulting in novel DNA sequences encoding the polypeptide or its derivatives. These modified sequences are used to produce mutant polypeptide and to directly express the polypeptide. Methods for saturating a particular DNA sequence with random mutations and also for making specific site directed mutations are known in the art, such as by treatment with a chemical mutagen, polymerase chain reaction, or other methods; see e.g. Sambrook et al supra, Chapter 15, incorporated herein by reference in its entirety.

As used herein, a "nonsense mutation" means a change in the DNA sequence that changes a codon in the mRNA that is normally translated as an amino acid into one that functions as a stop codon (5'-UAA, 5'-UAG, or 5'-UGA) that causes termination of translation. For example, the sequence 5'-TCA in DNA (transcribed to 5'-UCA in the mRNA) specifies the amino acid serine in the encoded protein. A mutation in which the 'C' is changed to 'A' (TCA to TAA; UCA to UAA in the mRNA) is a nonsense mutation since UAA is a stop codon.

As used herein, a "missense mutation" refers to a change in the DNA sequence that changes a codon in the MRNA that is normally translated as one amino acid into a codon that is translated as a different amino acid. For example, a mutation in which the 'C' in 5'-TCA is changed to 'T' (UCA to UUA in the mRNA) is a missense mutation. The serine encoded by the TCA codon would be replaced by leucine, the amino acid encoded by the TTA (UUA) codon, when the protein is synthesized in the cell. Some but not all missense mutations result in a non-functional gene-product. A selection method must be used to find those missense mutations that substantially affect the protein function.

Recombinant DNA constructs comprising one or more of the DNA or RNA sequences described herein and an additional DNA and/or RNA sequence are also included within the scope of this invention. These recombinant DNA constructs have sequences, which do not occur in nature or exist in a form that does not occur in nature or exist in association with other materials that do not occur in nature. The DNA and/or RNA sequences described hereinabove are "operably linked" with other DNA and/or RNA sequences. DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous (or in close proximity to) and, in the case of secretory leaders, contiguous and in the same reading frame.

The invention is further directed to a replicable vector containing cDNA for the upstream gene and/or downstream reporter gene. The present invention is also directed to a vector comprising a replicable vector and a DNA sequence corresponding to the above-described gene inserted into said vector. The vector may be an integrating or non-integrating vector and is conveniently a plasmid.

The invention further relates to a transformed cell or microorganism containing cDNA or a vector containing the translationally coupled genes thereof and which is capable of expressing the polypeptide.

A plethora of suitable microbial vectors are available. Generally, a microbial vector will contain an origin of replication recognized by the intended host, a promoter which will function in the host and typically, but not necessarily a phenotypic selection gene, for example, a gene encoding proteins conferring antibiotic resistance or supplying an auxotrophic requirement.

Vectors must contain a promoter, which is recognized by the host organism. This is generally a promoter homologous to the intended host. The promoter used may be the natural promoter of the upstream gene. Alternatively, recombinant promoters often used in recombinant DNA construction include the β-lactamase (penicillinase) and lactose promoter systems, a tryptophan (trp) promoter system and the tac promoter. While these are commonly used, other known microbial promoters are suitable. Details concerning their nucleotide sequences have been published, enabling a skilled worker to operably ligate them to DNA encoding the desired polypeptide in plasmid vectors and the DNA encoding the desired polypeptide.

Common prokaryotic host cells include bacteria such as E. coli.

Examples of useful mammalian host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment, which also contains the SV40 viral origin of replication. Smaller or larger SV40 fragments may also be used, provided the approximately 250 bp sequence extending from the Hind III site toward the BglI site located in the viral origin of replication is included.

An origin of replication may be provided either by construction of the vector to include an exogenous origin, such as may be derived from SV40 or other viral (e.g., Polyoma, Adenovirus, VSV, or BPV) source, or may be provided by the host cell chromosomal replication mechanism. If the vector is integrated into the host cell chromosome, the latter is often sufficient.

In plants, transformation vectors capable of introducing encoding DNAs are easily designed, and generally contain one or more DNA coding sequences of interest under the transcriptional control of 5' and 3' regulatory sequences. Such vectors generally comprise, operatively linked in sequence in the 5' to 3' direction, a promoter sequence that directs the transcription of a downstream heterologous structural DNA in a plant; optionally a 5' non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the MRNA encoding said protein. Plant transformation vectors also generally contain a selectable marker. Typical 5'-3' regulatory sequences include a transcription initiation start site, a ribosome binding site, an RNA processing signal, a transcription termination site, and/or a polyadenylation signal.

Plant promoter sequences can be constitutive or inducible, environmentally- or developmentally-regulated, or cell- or tissuespecific. Often-used constitutive promoters include the CaMV 35S promoter, the enhanced CaMV 35S promoter, the Figwort Mosaic Virus (FMV) promoter, the mannopine synthase (mas) promoter, the nopaline synthase (nos) promoter, and the octopine synthase (ocs) promoter. Useful inducible promoters include heat-shock promoters, a nitrateinducible promoter derived from the spinach nitrate reductase gene, hormone-inducible promoters, and light-inducible promoters associated with the small subunit of RuBP carboxylase and LHCP gene families. Examples of useful tissue-specific, developmentally regulated promoters include the β-conglycinin 7S promoter and seed specific promoters. Plant functional promoters useful for preferential expression in seed plastics include those from plant storage protein genes and from genes involved in fatty acid biosynthesis in oilseeds. Examples of such promoters include the 5'-regulatory regions from such genes as napin, phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffinan, U.S. Pat. No. 5,106,739), or to combine desired transcriptional activity and tissue specificity.

The following examples are offered by way of illustration of the present invention, and not by way of limitation.

EXAMPLES

Materials and Methods. T4 gene2 am mutant phage T4 2− was a gift from Dr. Gerald R. Smith, Fred Hutchinson Cancer Research Center, Seattle, WA. *E. coli* strain DPB273 (recD1905::mini-tet (tet$^r$) (Biek, D. P., and Cohen, S. N. (1986) *J. Bacteriol.* 167, 594–603)) was obtained from Dr. Stanley Cohen, Stanford University. Tetracycline, ampicillin and kanamycin were used at 12, 50, and 60 µg/ml, respectively.

Figure 1:
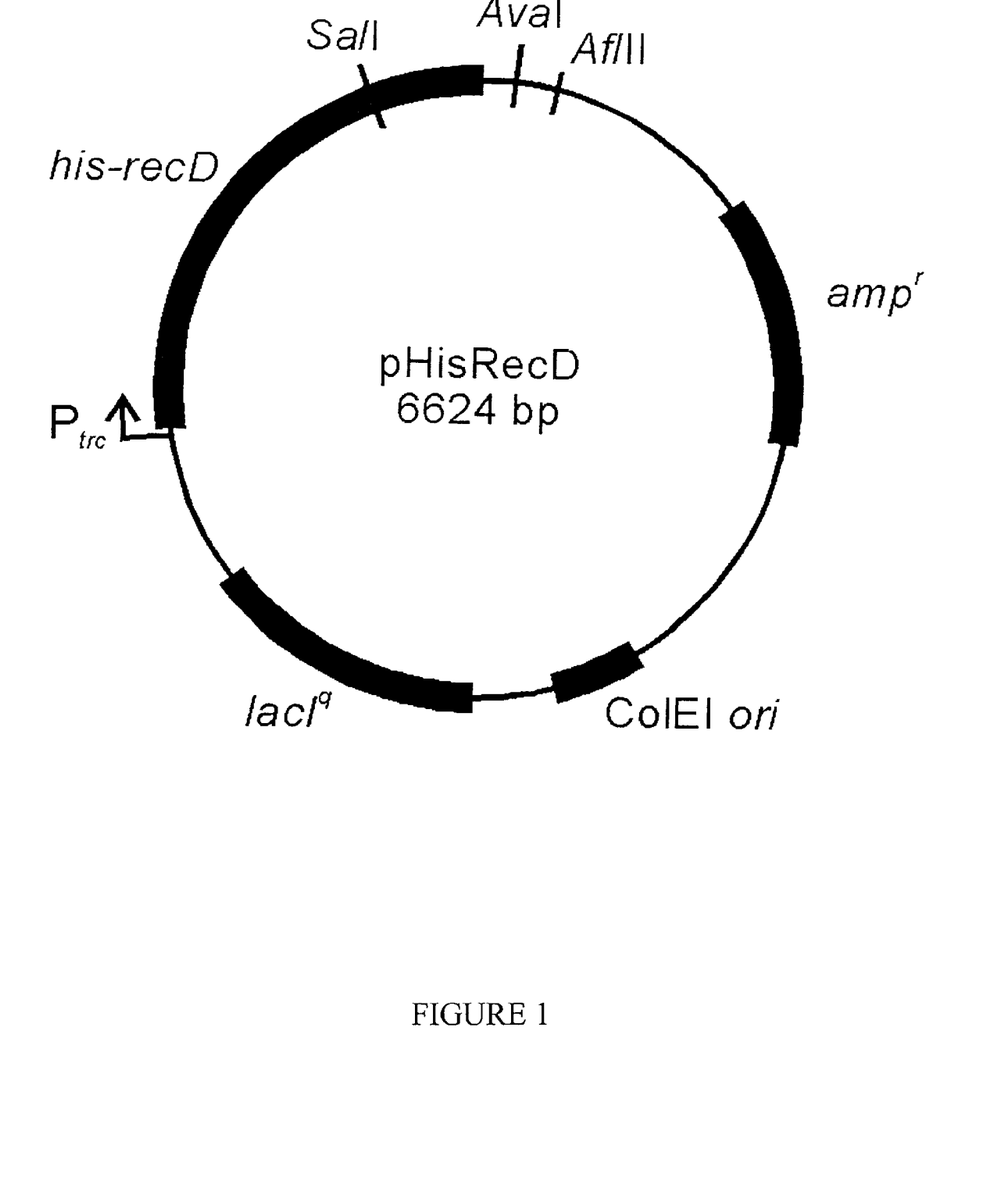
FIG. 1. Structure of pHisRecD.

Construction of the recD-kan$^r$ operon plasmid. The recD gene used in these experiments was previously inserted into the vector pTrcHisB (Invitrogen Corp.) to make pHisRecD (FIG. 1) (Chen, H.-W., Ruan, B., Yu, M., Wang, J., and Julin, D. A. (1997) *J. Biol. Chem.* 272, 10072–10079). The last 392 bp of the recD gene in pHisRecD (from the SalI site to the 3'-end; see FIG. 1) were amplified by PCR. The downstream primer altered the natural stop codon of recD (5'-TAA) to TGA and introduced an XbaI site after the stop codon. (The stop codon was altered so that the mRNA would form the hairpin structure shown in FIG. 2(B). The hairpin that could be formed by the original sequence would be less stable due to the absence of one GC base pair.) The amplified DNA product was digested with SalI and XbaI and the resulting 393 bp fragment was purified from a 0.6% agarose gel using the GeneClean II kit from Bio101 Corp.

The entire kan$^r$ gene (816 bp) in the plasmid pUC4K (Amersham Pharmacia Biotech) was also amplified by PCR. The upstream primer introduced an XbaI site and a ribosome binding site (AGGAGGT (Shine, J., and Dalgarno, L. (1974) *Proc. Natl. Acad. Sci.* USA 71, 1342–1346, incorporated herein by reference in its entirety)) before the 5'-end of the gene, while the downstream primer introduced an AflII site beyond the 3'-end of the gene. The amplified DNA product was digested with XbaI and AflII and the resulting 825 bp fragment was purified as above.

Figure 2A:
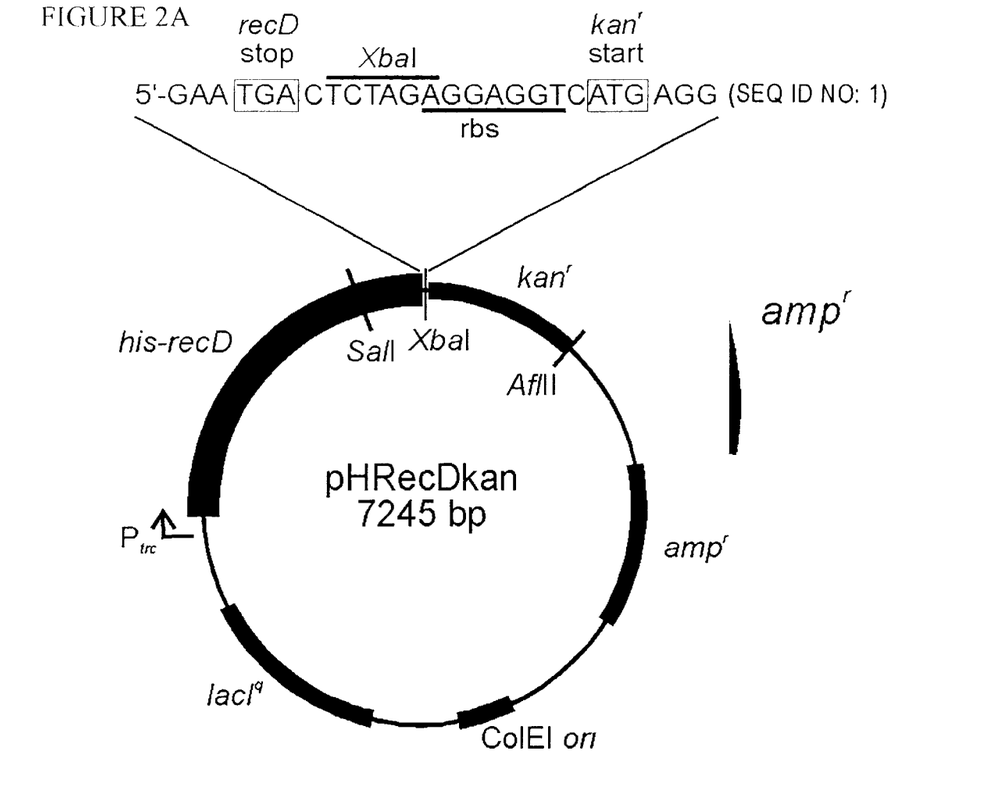
FIG. 2(A). Structure of pHRecDkan.
Figure 2B:
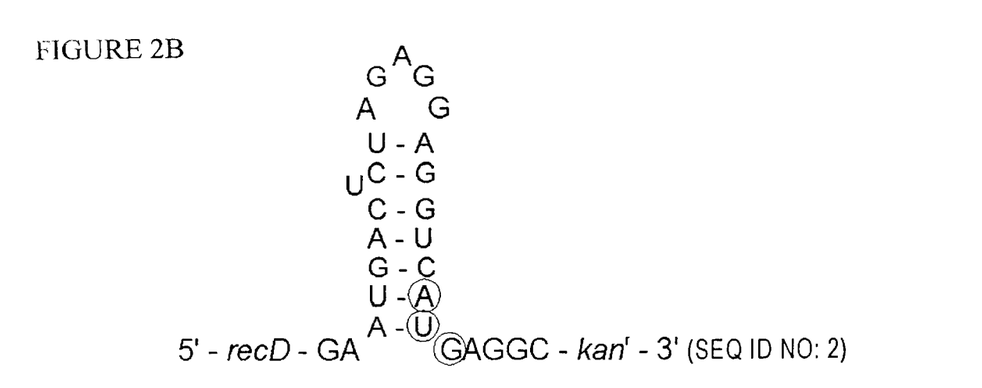

The two purified DNA fragments were then ligated to the 6023 bp SalI-AflII fragment from pHisRecD to produce pHRecDkan (FIG. 2A). The structure of the recD-kan$^r$ junction in pHRecDkan was confirmed by restriction digestion and by DNA sequencing.

Random Mutagenesis of the 3'-end of the recD Gene.

The DNA encoding the C-terminal 130 amino acid residues of RecD was mutagenized by PCR in either pHisRecD or in pHRecDkan. All PCR reactions contained 2–2.5 units of Taq DNA polymerase (Fisher Biotech), 1×Taq polymerase reaction buffer supplied with the enzyme, 50 pmoles of each primer, and 3.6–5 fmoles of circular plasmid template in a total volume of 50 µl. The reaction mixtures were subjected to 16 cycles of amplification: 94° C., 1 min (94° C., 5 min for the first cycle); 55° C., 1 min; 72 ° C., 6 min. The reaction volume was then adjusted to 200 µl with H$_2$O and Taq reaction buffer, all dNTP concentrations were increased to 0.2 mM (if possible), and the mixture was subjected to another 25 cycles: 94° C., 1 min; 55° C., 1 min; 72+ C., 1 min (final cycle 72° C., 5 min).

For pHisRecD, the sequence between the SalI and AvaI sites (FIG. 1) was amplified under the following mutagenic conditions (Fromant, M., Blanquet, S., and Plateau, P. (1995) *Anal. Biochem.* 224, 347–353, which is incorporated by reference herein in its entirety): 0.2 mM each of dATP and dCTP, 0.25 mM each of dGTP and dTTP, 1.1 mM MgCl$_2$, and 0.5 mM MnCl$_2$; or: 0.2 mM each of dATP, dTTP, and dCTP, 0.1 mM dGTP, and 0.9 mM MgCl$_2$. The amplified products were digested with SalI and Ava I and the 516 bp fragments obtained were ligated to the 6108 bp AvaI/SalI fragment from pHisRecD.

The DNA between the SalI and XbaI sites in pHRecDkan (FIG. 2A) was mutagenized using three different conditions: 1) 0.2 mM each of dATP, dGTP, and dTTP, 2 mM dCTP, 3.3 mM MgCl$_2$; 2) 0.2 mM dATP, 0.18 mM dGTP, 1.26 mM dTTP, 0.22 mM dCTP, 0.5 mM MnCl$_2$, 2.04 mM MgCl$_2$; 3) 0.56 mM dATP, 0.2 mM dGTP, 1.4 mM dTTP, 0.9 mM dCTP, 0.5 mM MnCl$_2$, 3.26 mM MgCl$_2$. The amplified products were digested with SalI and XbaI and the 393 bp fragments obtained were ligated to the 6852 bp XbaI/SalI fragment from pHRecDkan.

RecD mutant selection procedure. Mutagenized plasmids that could not complement the recD1905 mutation were selected using the "nibbled colony" assay (Chaudhury, A. M., and Smith, G. R. (1984) *Proc. Natl. Acad. Sci.* USA 81, 7850–7854), herein incorporated by reference in it entirety. When recD− cells (e. g., DPB273) are spread on agar plates containing a small number of T4 2− phage, the edges of the resulting colonies have a ragged appearance as the outskirts of the colony are attacked by the limited number of phage on the plate. A recD+cell (i. e., recBCD+) is impervious to T4 2− and thus forms a colony with a normal smooth perimeter. DPB273 containing either pHisRecD or pHRecDkan behaves like a wild-type cell in this assay (not shown).

The ligation mixtures from the mutagenic PCR reactions (see above) were transformed into DPB273, spread on LB plates (tryptone (10 g/l ), yeast extract (5 g/l), sodium chloride (10 g/l)) containing tetracycline, ampicillin, and T4 2− phage (10$^5$ pfu/plate), and incubated overnight at 37° C. Nibbled colonies were streaked twice on LB plates containing tetracycline and ampicillin to remove the infecting T4 2− phage. For DPB273 (pHRecDkan), the colonies were then toothpicked to LB plates containing ampicillin alone or containing both kanamycin and ampicillin to test for expression of the kan$^r$ gene.

The mutants obtained in both screens were tested for whether they express full-length HisRecD protein. HisRecD protein expression was induced by adding 1 mM isopropyl β-D-thiogalactopyranoside (IPTG) to a mid-log phase culture of DPB273 (pHisRecD) or DPB273 (pHRecDkan) in LB medium containing tetracycline and ampicillin. After 4 hours growth at 37° C., 250 µl of the culture was withdrawn, the cells were harvested by centrifugation, and the cell pellet was resuspended in 100 µl of 45 mM Tris-HCl, pH 6.8, 9% glycerol, 0.9% SDS, 130 mM β-mercaptoethanol, and 0.0024% bromophenol blue. This mixture was heated at 90° C. for 5 min and a 30 µl aliquot was subjected to SDS PAGE (10% polyacrylamide). The gel was stained with Coomassie Brilliant Blue R250 to visualize the protein.

Results and Discussion. We first prepared random mutations in the C-terminal region of recD in pHisRecD and looked for nibbled colonies in DPB273. Of approximately 4500 colonies, 58 were sensitive to the phage in this assay and thus were recD$^−$ mutants. However, analysis of crude cell extracts prepared from these colonies showed that only 15.5% of these potential mutants (9 of 58) produced a protein that was of the size expected for HisRecD (70 kDa). Extracts prepared from about half (53%) of the colonies contained a protein whose expression was greatly increased after induction with IPTG but that was smaller than HisRecD. These were most likely due to nonsense mutations that caused premature termination of translation and thus led to production of a protein smaller than the full-length HisRecD protein. The other colonies (31%) did not have any significantly overexpressed protein, presumably due to mutations that de-stabilized the folded structure of the HisRecD protein and caused it to be degraded rapidly in the cell.

The relatively low percentage of mutants that produced full-length HisRecD protein, and the necessity for analysis by SDS-PAGE, led us to develop an improved method for selecting against nonsense mutations. We sought to take advantage of the polar effects of nonsense mutations on transcription (Platt, T., and Bear, D. G. (1983) in Gene Function in Prokaryotes (Beckwith, J., Davies, J., and Gallant, J. A., Eds.), pp. 123–161, Cold Spring Harbor Laboratory, Cold Spring Harbor, N.Y., incorporated herein by reference in its entirety) and of translational coupling in a bicistronic message to discard nonsense mutations. Two genes are translationally coupled when the translation of the downstream gene depends on the complete translation of the upstream gene (Das, A., and Yanofsky, C. (1989) *Nucl. Acids Res.* 17, 9333–9340; Spanjaard, R. A., and van Duin, J. (1989) *Nucl. Acids Res.* 17 5501–5507; Londei, P. (1998) *Biochim. Biophys. Acta.* 1396, 169–178; Gold, L. (1988) *Annu. Rev. Biochem.* 57, 199–233). A premature stop codon within the upstream cistron that causes termination of its translation also prevents translation of the downstream coding region (Das, A., and Yanofsky, C. (1989) *Nucl. Acids Res.* 17, 9333–9340; Spanjaard, R. A., and van Duin, J. (1989) *Nucl. Acids Res.* 17 5501–5507).

Expression of the $kan^r$ gene in pHRecDkan depends on transcription initiation at the trc promoter and production of a bicistronic message encoding both his-recD and $kan^r$. The RNA sequence transcribed from the linker DNA connecting the 3'-end of his-recD to the 5'-end of the $kan^r$ gene has the potential to form a short stem-loop structure (FIG. 2B) that might inhibit translation initiation from the AUG codon for $kan^r$. Secondary structure in the mRNA in the vicinity of the downstream start codon can cause translation of the downstream gene to be coupled to the upstream gene, since a ribosome translating the 3'-end of the upstream gene disrupts the secondary structure and relieves the translation inhibition of the downstream gene. (Dallmann, H. G., and Dunn, S. D. (1994) *J. Bacteriol.* 176, 1242–1250; Rex, G., Surin, B., Besse, G., Schneppe, B., and McCarthy, J. E. (1994) *J. Biol. Chem.* 269, 18118–18127, incorporated herein by reference in its entirety). Thus, we anticipated that translation of the $kan^r$ coding region should be coupled to that of his-recD.

There were 77 nibbled colonies when the mutagenized pHRecDkan was transformed into DPB273 and spread on plates containing T4 $2^-$ phage and ampicillin but no kanamycin. These colonies were cured of the phage and transferred to a plate that contained only ampicillin and one that contained both ampicillin and kanamycin. All 77 colonies grew on the ampicillin plate, and 63 grew on the plate that contained both antibiotics. The HisRecD proteins expressed in these colonies were analyzed by SDS-PAGE (Table 1).

The results in Table 1 show that the downstream $kan^r$ reporter greatly enhances the efficiency of selecting for mutants that express full-length HisRecD protein. Most of the colonies that were kanamycin resistant (57 out of 63; 90%) also expressed full-length HisRecD. However, of the colonies that grew in the presence of ampicillin but that were sensitive to kanamycin ($amp^r$ $kan^s$) none (0 out of 14) expressed the full-length HisRecD protein. Thus the initial investment of time and effort to create pHRecDkan (two PCR reactions to place the $kan^r$ gene downstream of the his-recD gene) is made up for by the time and effort saved in screening the mutants. Although they must still be checked by SDS-PAGE or western blotting, a much greater fraction of colonies screened is likely to produce full-length mutant protein, and so the process is much more productive overall. This approach should be readily adaptable to random mutagenesis of most genes.

All of the references cited herein are incorporated by reference in their entirety.

TABLE 1

HisRecD proteins expressed in T4 2- sensitive colonies of DPB273(pHRecDkan).

| | # of colonies[a] | % | | # of colonies[b] | % |
|---|---|---|---|---|---|
| $amp^r kan^s$:<br>HisRecD protein expressed[c]: | 14 | 100 | $amp^r kan^r$: | 63 | 100 |
| full-length: | 0 | 0 | | 57 | 90.5 |
| truncated: | 4 | 28 | | 6 | 9.5 |
| unstable[d]: | 10 | 72 | | 0 | 0 |

[a]T4 2- sensitive DPB273 (pHRecDkan) strains that grew on LB + ampicillin but not on LB + ampicillin + kanamycin.
[b]T4 2- sensitive DPB273 (pHRecDkan) strains that grew on both LB + ampicillin and LB + ampicillin + kanamycin.
[c]The HisRecD protein that was expressed in each DPB273 (pHRecDkan) strain was analyzed by SDS-PAGE as described in Materials and Methods.
[d]No overexpressed protein was observed in the gel.

REFERENCE

1. Fromant, M., Blanquet, S., and Plateau, P. (1995) *Anal. Biochem.* 224, 347–353.
2. Vartanian, J.-P., Henry, M., and Wain-Hobson, S. (1996) *Nucl. Acids Res.* 24, 2627–2631.
3. Gottesman, S., Wickner, S., and Maurizi, M. R. (1997) *Genes & Devel.* 11, 815–823.
4. Friedrich, T., Roth, M., Hehn-Kruse, S., and Jeltsch, A. (1998) *Biol. Chem.* 379, 475–480.
5. Kostelidou, K., Jagura-Burdzy, G., and Thomas, C. M. (1998) *J. Mol. Biol.* 281, 453–463.
6. van den Ent, F. M., Vos, A., and Plasterk, R. H. (1998) *J. Virol.* 72, 3916–3924.
7. Shibata, H., Kato, H., and Oda, J. (1998) *Protein Eng.* 11, 467–472.
8. Oka, A., Sugisaki, H., and Takanami, M. (1981) *J. Mol. Biol.* 147, 217–226.
9. Das, A., and Yanofsky, C. (1989) *Nucl. Acids Res.* 17, 9333–9340.
10. Spanjaard, R. A., and van Duin, J. (1989) *Nucl. Acids Res.* 17 5501–5507.
11. Biek, D. P., and Cohen, S. N. (1986) *J. Bacteriol.* 167, 594–603.

12. Chen, H.-W., Ruan, B., Yu, M., Wang, J., and Julin, D. A. (1997) *J. Biol. Chem.* 272, 10072–10079.
13. Shine, J., and Dalgarno, L. (1974) *Proc. Natl. Acad. Sci. USA* 71, 1342–1346.
14. Chaudhury, A. M., and Smith, G. R. (1984) *Proc. Natl. Acad. Sci. USA* 81, 7850–7854.
15. Platt, T., and Bear, D. G. (1983) in Gene Function in Prokaryotes (Beckwith, J., Davies, J., and Gallant, J. A., Eds.), pp. 123–161, Cold Spring Harbor Laboratory, Cold Spring Harbor, N.Y.
16. Londei, P. (1998) *Biochim. Biophys. Acta.* 1396, 169–178.
17. Gold, L. (1988) *Annu. Rev. Biochem.* 57, 199–233.
18. Dallmann, H. G., and Dunn, S. D. (1994) *J. Bacteriol.* 176, 1242–1250.
19. Rex, G., Surin, B., Besse, G., Schneppe, B., and McCarthy, J. E. (1994) *J. Biol. Chem.* 269,18118–18127.

2. The method of claim 1, wherein the upstream missense mutant expresses full length upstream gene product.

3. The method of claim 1, wherein said reporter gene encodes a protein having fluorescent property, colorimetic property, or enzymatic property.

4. The method of claim 1, wherein said reporter gene is a selective marker gene.

5. The method of claim 1, wherein said reporter gene, upstream coding sequence or both, is eukaryotic.

6. The method of claim 1, wherein said reporter upstream gene, or both, is bacterial.

7. The method of claim 1, wherein mutant is introduced by polymerase chain reaction or chemical mutagens.

8. The method of claim 1, wherein said nucleic acid construct comprises a ribosome binding site between the upstream coding sequence gene and the downstream reporter.

What is claimed is:

1. A method of selecting for a missense mutant product comprising:
   (a) making a synthetic nucleic acid construct comprising an upstream coding sequence gene and a downstream reporter gene that are translationally coupled;
   (b) introducing mutations into the upstream gene, wherein step (a) and (b) may be performed in any order;
   (c) inserting the construct into a host cell;
   (d) selecting for a phenotype of the upstream coding sequence, which is different from the phenotype of the original upstream, and is caused by the mutation in the upstream coding sequence gene; and
   (e) selecting for the expression of the downstream coding sequence, wherein
      (i) a combination of the presence of the phenotype of the mutated upstream and expression of the downstream coding sequence gene product indicates that the mutation in the upstream coding sequence is a missense mutation, and wherein
      (ii) a combination of the presence of the phenotype of the mutated upstream and no expression of the downstream coding sequence gene product indicates that the mutation in the upstream coding sequence is a nonsense mutation.

9. The method of claim 4, wherein said selective marker gene is an antibiotic resistance gene or an auxotrophic marker.

10. The method according to claim 5, wherein said eukaryotic reporter gene or coding sequence is mammalian.

11. The method according to claim 5, wherein said eukaryotic reporter gene or coding sequence is from a plant.

12. The method according to claim 9, wherein said antibiotic resistance gene is kanamycin resistance gene.

13. The method according to claim 6, wherein said upstream is recD.

14. The method according to claim 8, wherein said ribosome binding site has the sequence 5'-AGGAGGU, 5'-GAGGGG, 5'-GGAG, 5'-GGUGGU, 5'-GGAGG or 5'-UAAGGAGGU.

15. The method according to claim 8, wherein said ribosome binding site forms part of a stem and loop structure with a nearby nucleotide sequence, wherein the stability of said stem and loop structure is optimized by arranging complementarity with the nearby nucleotide sequence in the stem structure so that a maximum number of base pairs is formed.

16. A method of selecting for and isolating a missense mutant gene product comprising:
   (a) making a synthetic nucleic acid construct comprising an upstream coding sequence and a downstream reporter gene that are translationally coupled;

(b) introducing mutations into the upstream coding sequence, wherein step (a) and (b) may be performed in any order;

(c) inserting the construct into a host cell;

(d) selecting for a phenotype of the upstream coding sequence, which is different from the phenotype of the original upstream coding sequence and is caused by the mutation in the upstream coding sequence;

(e) selecting for the expression of the downstream gene, wherein
   (i) a combination of the presence of the phenotype of the mutated upstream and expression of the downstream coding sequence gene product indicates that the mutation in the upstream coding sequence is a missense mutation, and wherein
   (ii) a combination of the presence of the phenotype of the mutated upstream and no expression of the downstream coding sequence gene product indicates that the mutation in the upstream coding sequence is a nonsense mutation; and (f) isolating the missense coding sequence product from the host cell exhibiting the properties of (e)(i) above.

17. The method of claim 16, wherein said mutatives are made by polymerase chain reaction or chemical mutagens.

18. The method of claim 16, wherein the nucleic acid construct comprises a recD gene, a ribosome binding site, and a kanamycin resistance gene.

* * * * *

UNITED STATES PATENT AND TRADEMARK OFFICE
CERTIFICATE OF CORRECTION

PATENT NO. : 6,391,641 B1
DATED : May 21, 2002
INVENTOR(S) : Douglas A. Julin et al.

It is certified that error appears in the above-identified patent and that said Letters Patent is hereby corrected as shown below:

<u>Title page,</u>
Item [75], Inventors, change the third inventor's name from "Ruiwu Wang" to
-- Ruiwu Chen --.

Signed and Sealed this

Tenth Day of December, 2002

JAMES E. ROGAN
*Director of the United States Patent and Trademark Office*